US006419643B1

(12) United States Patent
Shimada et al.

(10) Patent No.: US 6,419,643 B1
(45) Date of Patent: Jul. 16, 2002

(54) CENTRAL VENOUS CATHETER WITH HEAT EXCHANGE PROPERTIES (75) Inventors: Lynn M. Shimada, Orange; William J. Worthen, Coto de Caza; Scott M. Evans, Santa Ana; Xia Luo, Buena Park; Robert Pecor, Aliso Viejo; Blair D. Walker, Mission Viejo, all of CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/376,524

(22) Filed: Aug. 18, 1999

Related U.S. Application Data (63) Continuation-in-part of application No. 09/305,613, filed on May 5, 1999, now Pat. No. 6,368,304, which is a continuation-in-part of application No. 09/253,109, filed on Feb. 19, 1999, now abandoned, which is a continuation-in-part of application No. 09/063,984, filed on Apr. 21, 1998, now Pat. No. 6,126,684.

(51) Int. Cl.⁷ .......................... A61B 5/00; A61M 25/00
(52) U.S. Cl. ...................................... 600/585
(58) Field of Search .......................... 600/585; 607/106, 607/23, 105, 104; 606/34

(56) References Cited

U.S. PATENT DOCUMENTS

| 2,308,484 A | 1/1943 | Auzin et al. |
| 3,125,096 A | 3/1964 | Antiles et al. |
| 3,142,158 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato ........................ 128/400 |
| 3,504,674 A | 4/1970 | Swenson et al. |
| 3,738,372 A | 6/1973 | Shioshvili |
| 3,776,241 A | 12/1973 | Magilton |
| 3,897,790 A | 8/1975 | Magilton et al. |
| 3,913,581 A | 10/1975 | Ritson et al. |
| 4,010,795 A | 3/1977 | Stenberg ........................ 165/46 |
| 4,111,209 A | 9/1978 | Wolvek et al. ............... 128/400 |
| 4,154,245 A | 5/1979 | Daily |
| 4,249,923 A | 2/1981 | Walda |
| 4,298,006 A | 11/1981 | Parks |
| 4,416,280 A | 11/1983 | Carpenter et al. |
| 4,416,281 A | 11/1983 | Cooper et al. ............... 128/400 |
| 4,497,324 A | 2/1985 | Sullivan et al. ............. 128/736 |
| 4,546,759 A | 10/1985 | Solar ......................... 128/1 D |
| 4,583,969 A | 4/1986 | Mortensen |
| 4,662,383 A | 5/1987 | Sogawa et al. ............. 128/784 |
| 4,672,962 A | 6/1987 | Hershenson |
| 4,673,393 A | 6/1987 | Suzuki et al. |
| 4,745,922 A | 5/1988 | Taylor |
| 4,748,979 A | 6/1988 | Hershenson |
| 4,750,493 A | 6/1988 | Brader |
| 4,754,752 A | 7/1988 | Ginsburg et al. |
| 4,759,349 A | 7/1988 | Betz et al. |
| 4,791,930 A | 12/1988 | Suzuki et al. |

(List continued on next page.)

FOREIGN PATENT DOCUMENTS

| EP | 1 029 520 A1 | 8/2000 |
| WO | WO 91/05528 | 5/1991 |
| WO | WO 98/31312 | 4/1998 |
| WO | WO98/26831 | 6/1998 |
| WO | WO 98/44980 | 10/1998 |
| WO | WO 99/66970 | 12/1999 |

*Primary Examiner*—Kevin Shaver
*Assistant Examiner*—Brian Szmal
(74) *Attorney, Agent, or Firm*—John Rogitz; Arlyn Alonzo (57) ABSTRACT

An introducer sheath for a central venous catheter includes a sheath body and a temperature sensor mounted distally on the body. Either the catheter or sheath has a heat exchange region through which coolant is circulated to effect heat exchange with the body, with the coolant temperature being controlled in response to signals from the temperature sensor. Arterial dialysis heat exchange catheters and jugular bulb heat exchange catheters are also disclosed.

27 Claims, 4 Drawing Sheets

U.S. PATENT DOCUMENTS

| | | | | |
|---|---|---|---|---|
| 4,796,640 | A | 1/1989 | Webler | 128/736 |
| 4,813,210 | A | 3/1989 | Masuda et al. | |
| 4,819,655 | A | 4/1989 | Webler | 128/713 |
| 4,823,076 | A | 4/1989 | Haines et al. | |
| RE32,983 | E | 7/1989 | Levy | |
| 4,844,074 | A | 7/1989 | Kurucz | |
| 4,850,958 | A | 7/1989 | Berry et al. | |
| 4,860,744 | A | 8/1989 | Johnson et al. | |
| 4,883,455 | A | 11/1989 | Leonard | |
| 4,894,164 | A | 1/1990 | Polaschegg | |
| 4,899,741 | A | 2/1990 | Bentley et al. | |
| 4,901,734 | A | 2/1990 | Griffin et al. | 128/692 |
| 4,920,963 | A | 5/1990 | Brader | |
| 4,941,475 | A | 7/1990 | Williams et al. | |
| 4,987,896 | A | 1/1991 | Nakamatsu | |
| RE33,561 | E | 3/1991 | Levy | |
| 5,004,456 | A | 4/1991 | Botterbusch | 604/53 |
| 5,019,075 | A | 5/1991 | Spears et al. | |
| 5,021,045 | A | 6/1991 | Buckberg et al. | |
| 5,041,089 | A | 8/1991 | Mueller et al. | |
| 5,066,578 | A | 11/1991 | Wikman-Coffelt | |
| 5,078,713 | A | 1/1992 | Varney | |
| 5,092,841 | A | 3/1992 | Spears | |
| 5,098,376 | A | 3/1992 | Berry et al. | |
| 5,106,360 | A | 4/1992 | Ishiwara et al. | |
| 5,135,474 | A | 8/1992 | Swan et al. | 604/8 |
| 5,139,496 | A | 8/1992 | Hed | |
| 5,147,355 | A | 9/1992 | Friedman et al. | |
| 5,147,385 | A | 9/1992 | Beck et al. | |
| 5,151,100 | A | 9/1992 | Abele et al. | |
| 5,158,534 | A | 10/1992 | Berry et al. | |
| 5,174,285 | A | 12/1992 | Fontenot | |
| 5,182,317 | A | 1/1993 | Winters et al. | |
| 5,190,729 | A | 3/1993 | Hauenstein et al. | |
| 5,191,883 | A | 3/1993 | Lennox et al. | |
| 5,196,024 | A | 3/1993 | Barath | |
| 5,211,631 | A | 5/1993 | Sheaff | |
| 5,221,270 | A | 6/1993 | Parker | 604/282 |
| 5,230,862 | A | 7/1993 | Berry et al. | |
| 5,248,312 | A | 9/1993 | Langberg | |
| 5,250,070 | A | 10/1993 | Parodi | |
| 5,257,977 | A | 11/1993 | Eshel | |
| 5,259,839 | A | 11/1993 | Burns | 604/99 |
| 5,261,399 | A | 11/1993 | Klatz et al. | |
| 5,262,451 | A | 11/1993 | Winters et al. | |
| 5,269,758 | A | 12/1993 | Taheri | |
| 5,271,410 | A | 12/1993 | Wolzinger et al. | 128/692 |
| 5,275,595 | A | 1/1994 | Dobak, III | |
| 5,279,598 | A | 1/1994 | Sheaff | |
| 5,281,213 | A | 1/1994 | Milder et al. | |
| 5,281,215 | A | 1/1994 | Milder | |
| 5,286,254 | A | 2/1994 | Shima et al. | |
| 5,304,214 | A | * 4/1994 | DeFord et al. | 607/105 |
| 5,324,260 | A | 6/1994 | O'Neill et al. | 604/96 |
| 5,324,286 | A | 6/1994 | Fowle | |
| 5,338,770 | A | 8/1994 | Winters et al. | |
| 5,342,301 | A | 8/1994 | Saab | |
| 5,342,693 | A | 8/1994 | Winters et al. | |
| 5,354,277 | A | 10/1994 | Guzman et al. | |
| 5,370,616 | A | 12/1994 | Keith et al. | 604/102 |
| 5,382,234 | A | 1/1995 | Cornelius et al. | 604/96 |
| 5,411,477 | A | 5/1995 | Saab | |
| 5,423,807 | A | 6/1995 | Milder | |
| 5,437,637 | A | 8/1995 | Lieber et al. | 604/96 |
| 5,437,673 | A | 8/1995 | Baust et al. | |
| 5,452,582 | A | 9/1995 | Longsworth | |
| 5,478,309 | A | 12/1995 | Sweezer et al. | |
| 5,486,204 | A | 1/1996 | Clifton | 607/96 |
| 5,486,208 | A | 1/1996 | Ginsburg | |
| 5,531,776 | A | 7/1996 | Ward et al. | 607/105 |
| 5,542,928 | A | 8/1996 | Evans et al. | 604/113 |
| 5,545,134 | A | 8/1996 | Hilaire et al. | 604/96 |
| 5,545,137 | A | 8/1996 | Rudie et al. | 604/96 |
| 5,545,161 | A | 8/1996 | Imran | |
| 5,549,552 | A | 8/1996 | Peters et al. | 604/96 |
| 5,549,559 | A | 8/1996 | Eshel | |
| RE35,352 | E | 10/1996 | Peters | 604/4 |
| 5,562,606 | A | 10/1996 | Huybregts | |
| 5,595,181 | A | 1/1997 | Hubbard | 128/692 |
| 5,596,995 | A | 1/1997 | Sherman et al. | 128/736 |
| 5,609,620 | A | 3/1997 | Daily | |
| 5,624,302 | A | 4/1997 | Saab | |
| 5,634,720 | A | 6/1997 | Gallup et al. | 374/183 |
| 5,655,548 | A | 8/1997 | Nelson et al. | |
| 5,656,420 | A | 8/1997 | Chien | |
| 5,693,032 | A | 12/1997 | Bierman | |
| 5,693,080 | A | 12/1997 | Wallstén et al. | |
| 5,701,905 | A | * 12/1997 | Esch | 600/585 |
| 5,702,435 | A | 12/1997 | Maytal | |
| 5,733,319 | A | 3/1998 | Neilson et al. | |
| 5,735,809 | A | 4/1998 | Gorsuch | |
| 5,755,756 | A | 5/1998 | Freedman, Jr. et al. | 607/110 |
| 5,758,505 | A | 6/1998 | Dobak, III et al. | |
| 5,759,182 | A | 6/1998 | Varney et al. | |
| 5,776,176 | A | 7/1998 | Rudie | 607/101 |
| 5,787,715 | A | 8/1998 | Dobak, III et al. | |
| 5,800,375 | A | 9/1998 | Sweezer et al. | 604/4 |
| 5,800,486 | A | 9/1998 | Thome et al. | 607/105 |
| 5,800,493 | A | 9/1998 | Stevens et al. | 607/113 |
| 5,833,688 | A | 11/1998 | Sieben et al. | 606/41 |
| 5,861,021 | A | 1/1999 | Thome et al. | 607/101 |
| 5,868,735 | A | 2/1999 | Lafontaine | 606/21 |
| 5,879,329 | A | 3/1999 | Ginsburg | |
| 5,879,347 | A | 3/1999 | Saadat | 606/28 |
| 5,902,268 | A | 5/1999 | Saab | 604/96 |
| 5,902,299 | A | 5/1999 | Jayaraman | 606/20 |
| 5,906,588 | A | 5/1999 | Safar et al. | 604/64 |
| 6,024,740 | A | * 2/2000 | Lesh et al. | 606/34 |
| 6,042,559 | A | 3/2000 | Doba | |
| 6,096,068 | A | * 8/2000 | Dobak, III et al. | 607/105 |

* cited by examiner

CENTRAL VENOUS CATHETER WITH HEAT EXCHANGE PROPERTIES

RELATED APPLICATION

This application is a continuation-in-part of U.S. patent application Ser. No. 09/305,613, filed May 5, 1999 now U.S. Pat. No. 6,368,304 which is a continuation-in-part of U.S. patent application Ser. No. 09/253,109, filed Feb. 19, 1999 now abandoned which is a continuation-in-part of U.S. patent application Ser. No. 09/063,984, filed Apr. 21, 1998 now U.S. Pat. No. 6,126,684, all of which are incorporated herein by reference.

FIELD OF THE INVENTION

The present invention relates generally to methods and apparatus for cooling patients for therapeutic purposes, and more particularly to systems for establishing central venous access while providing a means for cooling a patient.

BACKGROUND

It has been discovered that the medical outcome for a patient suffering from severe brain trauma or from ischemia caused by stroke or heart attack is degraded if the patient's body temperature rises above normal (38°C.). It is further believed that the medical outcome for many such patients might be significantly improved if the patients were to be cooled relatively quickly for a short period, e.g., 24–72 hours. Apart from the therapeutic benefits of hypothermia, the outcomes for brain trauma or ischemia patients that develop fevers is worse than for patients that do not develop fevers. Consequently, temperature management for such patients is important, even when hypothermia is not to be used to treat the patients. Moreover, prophylactic short-term hypothermia might help patients undergoing minimally invasive heart surgery and aneurysm surgery.

The affected organ, in any case, is the brain. Accordingly, systems and methods have been disclosed that propose cooling blood flowing to the brain through the carotid artery. An example of such systems and methods is disclosed in co-pending U.S. patent app. Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. patent app. Ser. No. 09/133,813, filed Aug. 13, 1998, owned by the present assignee and incorporated herein by reference, the above-mentioned advantages in treating brain trauma/ischemic patients by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system.

Moreover, since many patients already are intubated with central venous catheters for other clinically approved purposes anyway, providing a central venous catheter that can also cool the blood, if only to manage temperature and thereby ameliorate fever spikes, requires no additional surgical procedures for those patients. A cooling central venous catheter is disclosed in the present assignee's co-pending U.S. patent application Ser. No. 09/253,109, filed Feb. 19, 1999 and incorporated herein by reference. The present inventions are directed to central venous cooling devices.

SUMMARY OF THE INVENTION

An introducer sheath for a central venous line catheter includes a hollow body defining a proximal end, a distal end positionable in a patient, and at least one catheter placement lumen extending therebetween. A barrier such as a septum or hemostasis valve is in the lumen at or near the proximal end of the body for selectively blocking the lumen, and at least one temperature sensor such as a thermistor or thermocouple is mounted on the body at or near the distal end for generating a temperature signal. The catheter can include at least one distally-located cooling membrane.

If desired, the body of the sheath further includes a coolant supply lumen and a coolant return lumen. Both the coolant supply lumen and coolant return lumen communicate with a distally-located heat transfer region associated with the body. The heat transfer region can be established by at least one membrane that is attached to the body, or by at least one distally-located fluid passageway that is formed in the body.

In another aspect, an introducer sheath for a central venous line catheter includes a hollow body defining a proximal end, a distal end positionable in a patient, and at least one catheter placement lumen extending therebetween. The body also defines a coolant supply lumen and a coolant return lumen. A barrier is disposed in the catheter placement lumen at or near the proximal end of the body for selectively blocking the catheter placement lumen, and a distally-located heat transfer region is associated with the body in communication with the coolant supply and return lumens.

In yet another aspect, a jugular vein catheter system includes a catheter body bearing at least one oxygen sensor connected to an optical fiber. An oxygen measuring system is connected to the fiber, and a heat exchange region is associated with a distal segment of the catheter body.

In still another aspect, an arterial catheter system includes a catheter body bearing at least one blood lumen, and a dialysis system communicating with the blood lumen. A heat exchange region is associated with a distal segment of the catheter body.

In another aspect, a heat exchange catheter includes a catheter body defining at least a coolant supply lumen, a coolant return lumen, and an air lumen. A cooling membrane defines a chamber that communicates with the coolant supply and return lumens, and an inflation balloon is disposed in the chamber. The inflation balloon is selectively movable between an inflated configuration, wherein the inflation balloon causes coolant to flow near an outer surface of the cooling membrane to thereby effect relatively greater heat exchange with the blood, and a deflated configuration, wherein coolant tends to flow through the cooling membrane with a laminar flow characteristic nearer the catheter body than the outer surface of the cooling membrane.

In still another aspect, a central venous access system includes a multi-lumen catheter, at least one heat exchange membrane or balloon located distally on the catheter and communicating with at least one coolant lumen of the catheter, and a heat exchange system communicating with at least the coolant lumen. Coolant is circulated between the heat exchange system and the membrane or balloon to effect heat exchange with a patient. At least one holder is engageable with the catheter to hold the catheter onto a patient. Also, a central venous system communicates with at least one lumen of the catheter.

The present invention also discloses an improvement to a Foley catheter configured for placement in the urinary tract of a patient. The improvement includes at least one heat exchange membrane or balloon located distally on the catheter body and communicating with at least one coolant lumen of the catheter. A heat exchange system communicates with at least the coolant lumen, with coolant being circulated between the heat exchange system and the membrane or balloon to effect heat exchange with a patient.

Moreover, a method is disclosed for heat exchange with a patient. The method includes advancing a catheter into the urinary tract of a patient, and circulating saline through the catheter in a closed loop to exchange heat with the patient.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
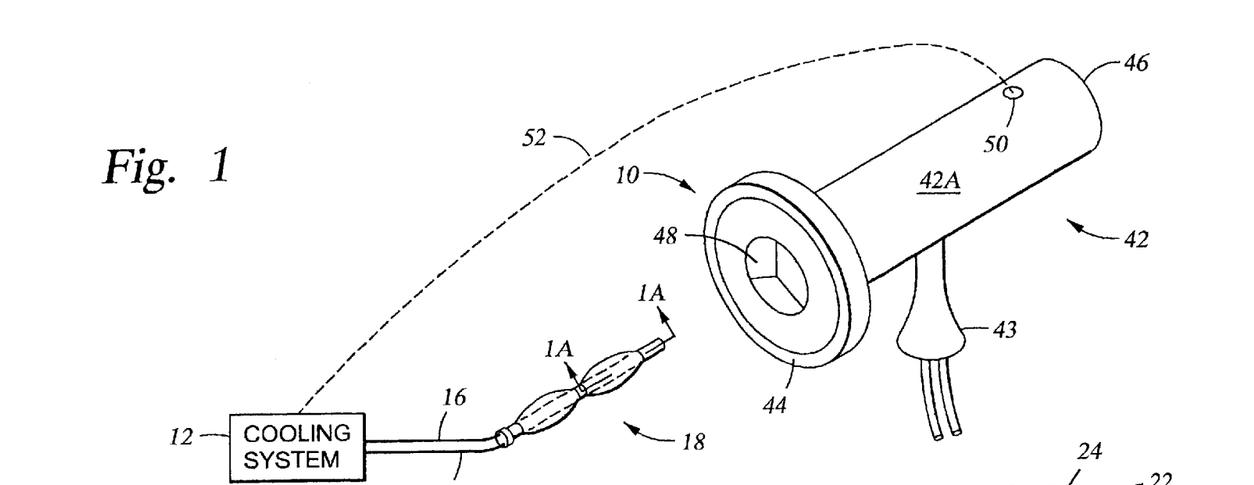
FIG. 1 is an exploded perspective view of a first embodiment of an entry sheath for a venous catheter, schematically showing a cooling system in communication with the catheter.

Referring initially to FIG. 1, a therapeutic catheter system, generally designated 10, is shown for establishing and maintaining hypothermia in a patient, or for attenuating a fever spike in a patient and then maintaining normal body temperature in the patient, or for returning a hypothermic patient to normothermic. Commencing the description of the system 10 at the proximal end, as shown the system 10 includes a cooling system 12 that can be a water-bath system or a TEC-based system such as either of the systems disclosed in co-pending U.S. patent application Ser. No. 09/220,897, filed Dec. 24, 1998 and incorporated herein by reference, or U.S. patent application Ser. No. 09/260,950, filed Mar. 2, 1999, also incorporated herein by reference. In any case, the coolant system 12 provides coolant such as saline water through a coolant supply line 14, and coolant is returned to the source 12 via a coolant return line 16. A catheter, generally designated 18, includes respective coolant supply and return lumens that communicate with the lines 14, 16 to establish a closed circuit coolant path between the catheter 18 and coolant source 12.

In one preferred embodiment, the catheter 18 is any one of the catheters disclosed in the above-referenced priority applications, incorporated herein by reference. For example, the catheter 18 can be the catheter disclosed in U.S. patent application Ser. No. 09/253,109, filed Feb. 19, 1999, which catheter includes a holder 18a to hold the catheter onto a patient for long-term intubation. The above-referenced application discloses an exemplary anchor that can establish the holder 18a. In addition to the structure disclosed in the above-referenced application, the in-growth flange set forth in U.S. Pat. No. 4,578,063 can be used as the present holder, or the anchoring systems set forth in U.S. Pat. Nos. 5,693,032 or 5,192,274 can be used, or the anchoring tape set forth in U.S. Pat. No. 3,677,250 can be used, or suture thread can be wound around the catheter body and attached to the patient to establish the holder. All of the above-referenced patents are incorporated herein by reference. Also, one or more central venous systems 19 communicate with one or more lumens of the catheter 18 via respective tubes 19a (only a single system 19 shown for clarity). The central venous system 19 can be, e.g., a source of medicament to be infused into a patient's central venous system, or a syringe or other device for extracting central venous blood from a patient, or a pressure monitoring or blood gas monitoring or temperature monitoring system.

Figure 1A:
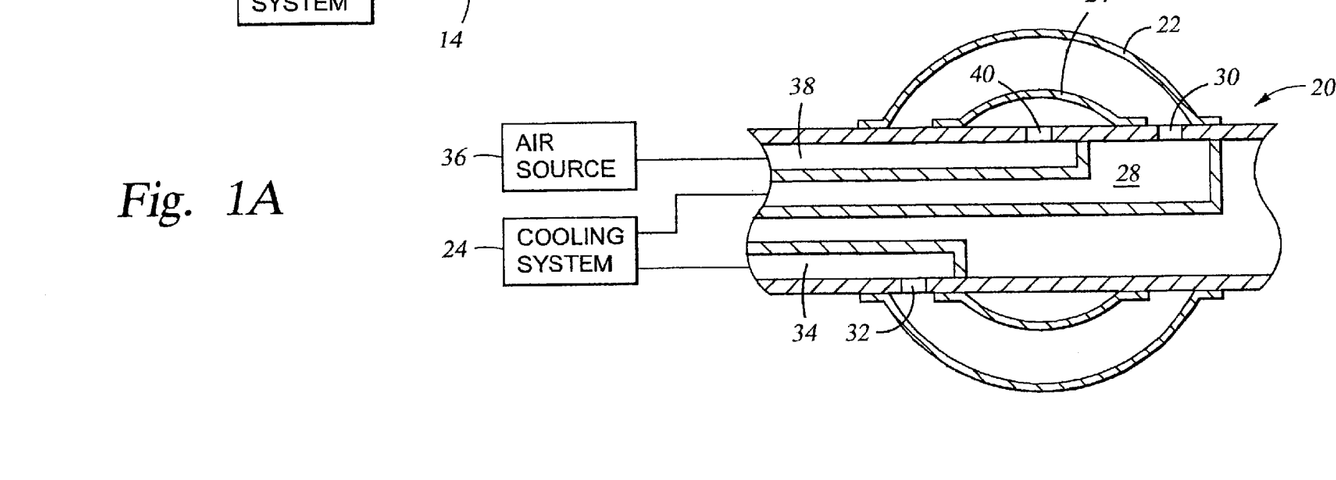
FIG. 1A is a longitudinal cross-section as would be seen along the line 1A—1A in FIG. 1, of an alternate balloon configuration for the catheter shown in FIG. 1.

Alternatively, the catheter 18 can be the modified catheter 20 shown in FIG. 1A, which in all essential respects is identical to the two-balloon catheter set forth in U.S. patent application Ser. No. 09/305,613, filed, May 5, 1999, with the following exceptions.

As shown in FIG. 1A, each of the two cooling balloons (only a single cooling balloon 22 is shown for clarity of disclosure) of the catheter 20 surrounds a respective inflation balloon 24. Coolant from a cooling system 26 or other coolant source enters each cooling balloon 22 through a coolant supply lumen 28 and coolant supply port or ports 30 and exits the cooling balloon 22 through a coolant exit port or ports 32 and coolant return lumen 34.

Additionally, inflation fluid such as air can be directed into the inflation balloon 24 from an air source 36 through an inflation lumen 38 and air port or ports 40 to inflate the inflation balloon 24. Air can be exhausted from the inflation balloon 24 back though the inflation lumen 38 to collapse the inflation balloon 24. With this structure, the inflation balloon 24 can be selectively moved between an inflated configuration (shown), wherein the inflation balloon 24 causes coolant to flow near the outer surface of the respective cooling balloon 22 and thereby effect relatively greater heat exchange with the blood, and a deflated configuration, wherein coolant tends to flow through the cooling balloon 22 with a laminar flow characteristic nearer the body of the catheter 20 than the outer surface of the catheter.

Referring back to FIG. 1, the catheter 18 can be introduced into a patient through an elongated hollow plastic introducer sheath 42 having a hollow body 42A and a side port 43 connected to the body 42A. The sheath 42 preferably is coated with an anti-microbial agent, and it can also be coated with an anti-clotting substance such as heparin.

As shown, the sheath 42 includes a proximal end 44 and an open distal end 46, it being understood that a working lumen through which the catheter 18 (or other catheter, conventional or otherwise) can be advanced extends between the proximal end 44 and distal end 46 of the sheath 42. A barrier 48 such as a septum or hemostasis valve or other barrier selectively blocks the working lumen. The catheter 18 can be advanced through the barrier 48, with the barrier 48 sealing against the catheter 18. Upon removal of the catheter 18, the barrier 48 closes to prevent backflow through the working lumen out of the proximal end 44 of the sheath 42.

In the preferred embodiment shown, a temperature sensor 50 is mounted on the sheath 42 at or near the distal end 46 to sense the temperature of blood flowing past the distal end 46. The sensor 50 can be a thermistor or thermocouple or other suitable temperature sensing device. In any case, the sensor 50 is operably connected to the cooling system 12 as schematically indicated by the dashed line 52, to provide temperature feedback to the system 12. This connection can be made by wireless transmission or through a wire or fiber that extends through the wall of the sheath 42. The sensor 50 can be mounted on the sheath 42 by solvent bonding or disposed in a lumen of the sheath 42, or attached to a wire that is disposed in a lumen of the sheath 42, with the sensor hanging outside the sheath 42.

Figure 2:
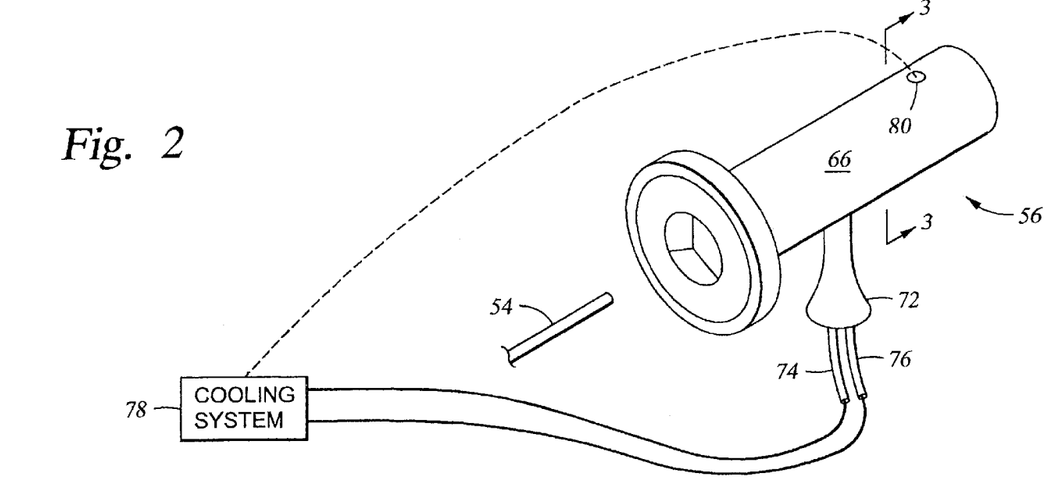
FIG. 2 is a perspective view of a second embodiment of the entry sheath, configured for providing cooling capability in a patent's central venous system.

FIG. 2 shows that instead of a cooling catheter 18/20, a non-cooling catheter 54 such as a conventional central venous catheter or a Swan-Ganz catheter as exemplified in U.S. Pat. No. 3,995,623 can be provided. In this case, a sheath 56 which is in all essential respects identical to the sheath 42 shown in FIG. 1, with the following exceptions, can be provided. The sheath 56 includes a central working lumen 58 (FIG. 3) for receiving the catheter 54 therein in slidable engagement, and at least along a distal segment of the sheath 56 coolant supply and return lumens 60, 62 surround the working lumen 58 to establish a distally-located heat transfer region. Accordingly, in the embodiment shown in FIGS. 2 and 3 a heat transfer region is established by at least one distally-located fluid passageway (e.g., either or both of the lumens 60, 62) that is formed in the body 66 of the sheath 56.

Figure 3:
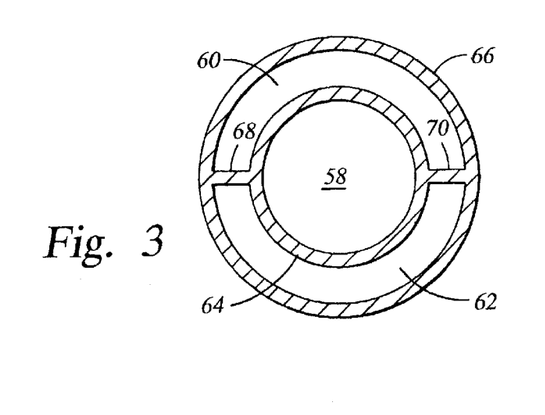
FIG. 3 is a cross-sectional view as seen along the line 3—3 in FIG. 2.

As shown best in FIG. 3, the working lumen 58 is defined by a central lumen wall 64, with the supply and return lumens 60, 62 being established between the wall 64 and an outer wall 66 of the sheath 56. Separator ribs 68, 70 extend laterally between the walls 64, 66 along the length of the coolant supply and return lumens 64, 66 to separate the coolant supply and return lumens 60, 62.

In accordance with the present invention, the coolant supply and return lumens 60, 62 communicate, via a side port 72 having supply and return tubes 74, 76, with a cooling system 78 that is in all essential respects identical to the system 12 shown in FIG. 1. If desired, a temperature sensor 80 can be mounted on the sheath 56 to provide temperature feedback to the cooling system 78 in accordance with principles set forth above.

Figure 3A:
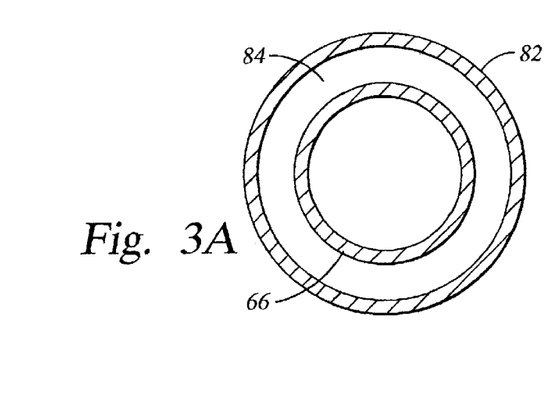
FIG. 3A is a cross-sectional view of an alternate sheath that includes a distal cooling balloon, as would be seen along the line 3—3 in FIG. 2.

Alternatively, as shown in FIG. 3A a thin-walled cooling balloon or membrane 82 can surround a distal segment of the outer wall 66 of the sheath 56, to establish a cooling chamber 84 between the outer wall 66 and the balloon or membrane 82. The embodiment of the sheath 56 shown in FIG. 3A would then function essentially analogously to the cooling catheters disclosed in the above-referenced patent applications, with the coolant from the system 78 entering and exiting the chamber 84 through respective coolant supply and return passageways in the sheath 56. In the embodiment shown in FIG. 3A, the distally-located heat transfer region is established by the balloon or membrane 82.

Figures 4, 5:
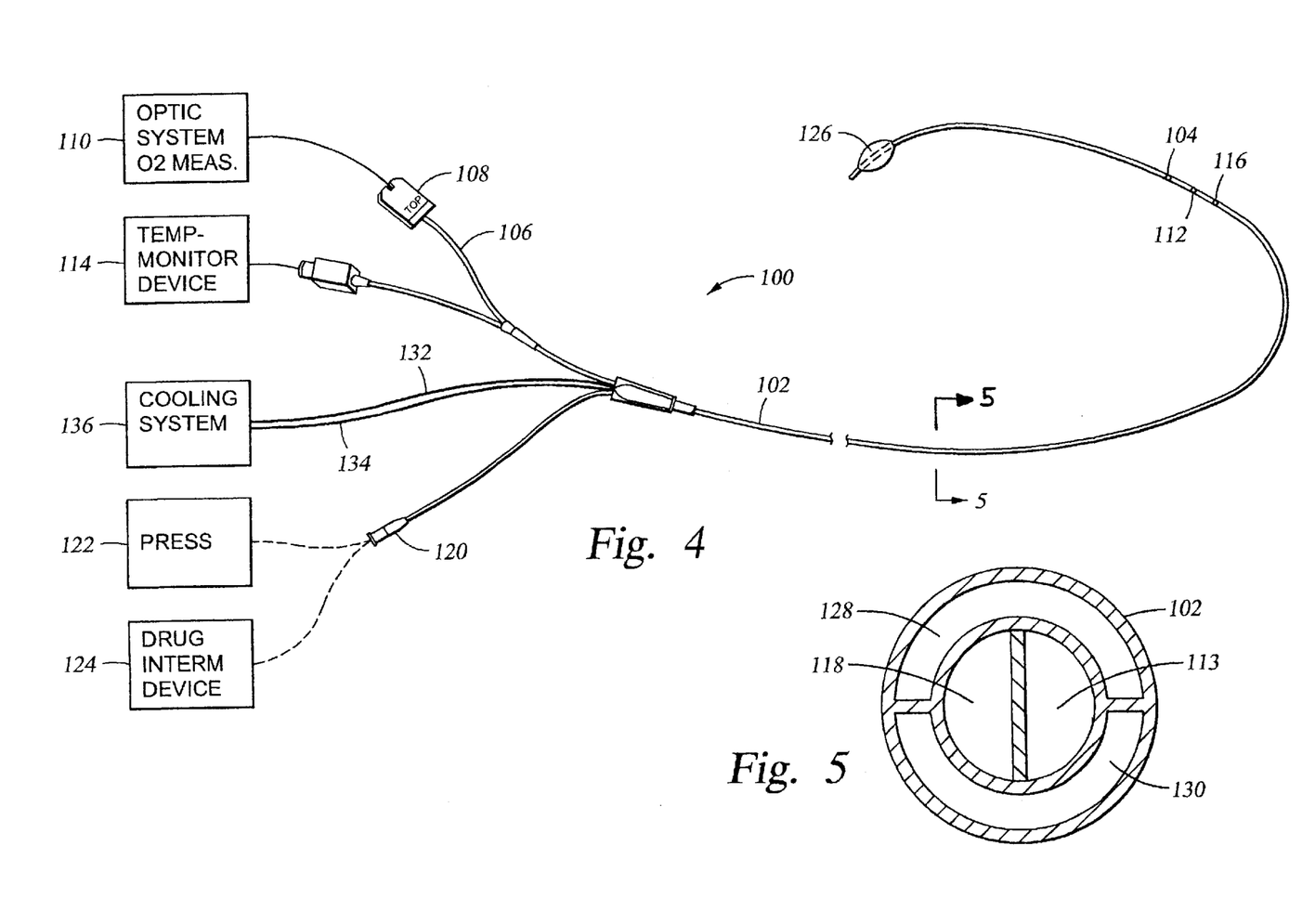
FIG. 4 is a perspective view of a so-called jugular bulb catheter configured for cooling a patient, schematically showing various jugular bulb components and a cooling system connected to the catheter.
FIG. 5 is a cross-sectional view as seen along the line 5—5 in FIG. 4.

Now referring to FIGS. 4 and 5, a jugular vein catheter system, generally designated 100, includes a jugular catheter body 102 bearing an oxygen sensor, shown schematically at 104. The jugular catheter can be the fiberoptic intravascular catheter sold under the trademark "Opticath" by Abbot Critical Care Systems, or a jugular catheter made by Baxter International, with the exceptions noted below.

An optical fiber 106 is connected to the oxygen sensor 104, and the fiber 106 terminates in an optical connection 108. In turn, the connector 108 can be connected to an oxygen measuring system 110. Further, a temperature sensor, shown schematically at 112, is supported by the body and is operably connected through a sensor lumen 113 (FIG. 5) with a monitoring system 114. Both the oxygen and temperature sensor connecting lines can extend through the sensor lumen 113. Moreover, a pressure sensor, shown schematically at 116, is supported on the body 102, and the pressure sensor 116 communicates via a pressure/infusion lumen 118 and luer-like fitting 120 with a pressure sensing system 122 or with a drug infusion device 124, such as a syringe or IV bag.

Unlike conventional jugular bulb catheters, however, the catheter 102 shown in FIGS. 4 and 5 includes a distally-located balloon or membrane 126. The balloon or membrane 126 is attached to the catheter body and communicates with coolant supply and return lumens 128, 130 that are formed in the catheter body. In turn, the coolant lumens 128, 130 communicate via coolant supply and return lines 132, 134 with a cooling system 136. With this structure, coolant can be circulated in the balloon or membrane 126 to effect heat exchange with a patient's body.

Figures 6, 8:
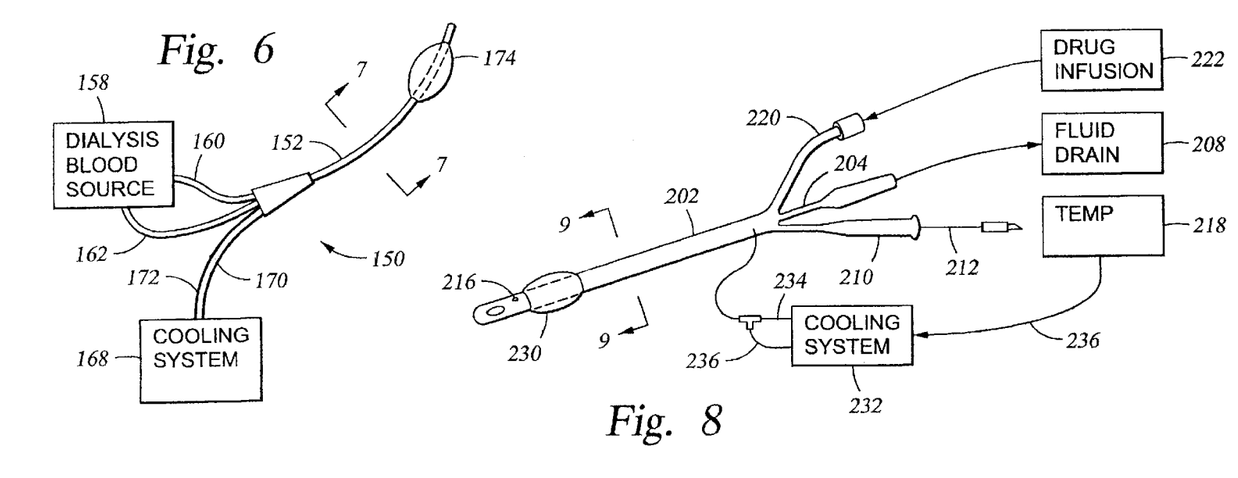
FIG. 6 is a perspective view of a dialysis catheter configured for cooling a patient, schematically showing various dialysis components and a cooling system connected to the catheter.
FIG. 8 is a perspective view of a Foley catheter configured for cooling a patient, schematically showing various Foley catheter components and a cooling system connected to the catheter.
Figure 7:
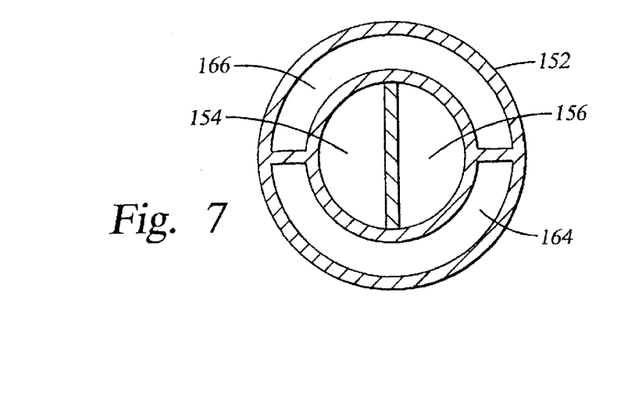
FIG. 7 is a cross-sectional view as seen along the line 7—7 in FIG. 6.

In addition to the above heat exchange structures, an arterial catheter system, generally designated 150 in FIGS. 6 and 7, can be provided to effect heat exchange with a patient. The system 150 includes an arterial catheter body 152. In accordance with arterial catheter principles, the body 152 includes a blood supply lumen 154 and a blood return lumen 156, both of which communicate with a dialysis blood source 158 via blood supply and return tubes 160, 162 for undertaking dialysis of a patient's blood.

As intended by the present invention, the arterial catheter system 150 also includes a heat exchange region associated with a distal segment of the catheter body 152. The body 152 includes coolant supply and return lumens 164, 166 that communicate with a cooling system 168 via supply and return tubes 170, 172, with the lumens 164, 166 establishing the heat exchange region. Or, the heat exchange region can be established by at least one distally-located balloon or membrane 174 that communicates with the supply and return lumens 166, 168 in accordance with present principles.

Figure 9:
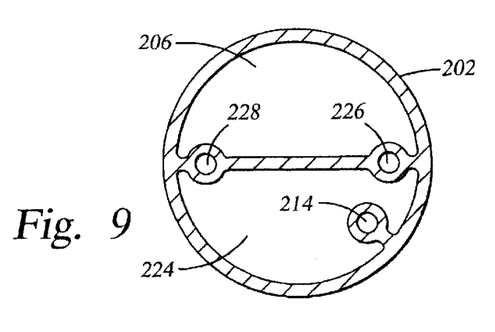
FIG. 9 is a cross-sectional view as seen along the line 9—9 in FIG. 8.

FIGS. 8 and 9 show a Foley catheter, generally designated 200, that is adapted for use for cooling the interior of a patient's bladder, to effect patient cooling. As shown, the catheter 200 includes a flexible resilient catheter body 202 terminating in a central fluid drainage tube 204 that communicates with a urine drainage lumen 206 (FIG. 9) in the body 202. The drainage tube 204 can be connected to a fluid collection receptacle 208 in accordance with Foley catheter principles known in the art. Also, the body 202 terminates in a temperature connector tube 210, and a temperature lead 212 extends through the connector tube 210 and a temperature lead lumen 214 (FIG. 9) for connecting a temperature sensor 216 that is distally located on the body 202 with a temperature monitor system 218. Moreover, a drug infusion tube 220 can be connected to a drug infusion source 222 to infuse drugs into the bladder of a patient through the drug infusion tube 220 and a drug infusion lumen 224 that communicates with the drug infusion tube 220.

In addition to the conventional Foley catheter structure described above, the catheter 200 shown in FIGS. 8 and 9 includes coolant supply and return lumens 226, 228 that communicate with at least one balloon or membrane 230 that is distally located on the catheter body 202 in accordance with principles set forth above. Coolant such as saline from a cooling system 232 is circulated through coolant supply and return lines 234, 236, coolant lumens 226, 228, and balloon or membrane 230 in a closed loop to remove heat from a bladder of a patient into which the catheter 200 has been advanced. It is to be understood that while FIG. 9 illustrates one lumen design layout, other layouts can be used. It is to be further understood that the cooling system 232 is in all essential respects identical in operation and construction to the above-described cooling systems. If desired, the temperature monitor system 218 can be connected to the cooling system 232 as indicated at the line 236 to provide temperature feedback to the cooling system 232.

While the particular CENTRAL VENOUS CATHETER WITH HEAT EXCHANGE MEMBRANE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. □112, sixth paragraph, unless the element is expressly recited using the phrase "means for".

What is claimed is:

1. An introducer sheath for a central venous line catheter, comprising:

a hollow body defining a proximal end, a distal end adapted to be positioned in a patient, and at least one lumen extending therebetween;

said hollow body further comprising at least one coolant lumen and at least one membrane communicating with the at least one coolant lumen;

a barrier in the lumen at or near the proximal end of the body for selectively blocking the lumen; and at least one temperature sensor mounted on the body at or near the distal end for generating a temperature signal.

2. The sheath of claim 1, wherein the barrier is a septum.

3. The sheath of claim 1, wherein the temperature sensor is thermistor or thermocouple.

4. The sheath of claim 1, in combination with the catheter.

5. The sheath of claim 4, wherein the catheter includes at least one distally-located cooling membrane.

6. The sheath of claim 1, wherein the body further includes a coolant supply lumen and a coolant return lumen, both the coolant supply lumen and coolant return lumen communicating with a distally-located heat transfer region associated with the body.

7. The sheath of claim 6, wherein the heat transfer region is established by at least one membrane attached to the body.

8. The sheath of claim 6, wherein the heat transfer region is established by at least one distally-located fluid passageway formed in the body.

9. The sheath of claim 1, wherein the barrier is a hemostasis valve.

10. An introducer sheath, comprising:

a hollow body defining a proximal end, a distal end adapted to be positioned in a patient, and at least one first lumen extending therebetween, the body also defining a coolant supply lumen and a coolant return lumen;

said hollow body further comprising at least one membrane communicating with the coolant supply lumen;

a barrier in the first lumen at or near the proximal end of the body for selectively blocking the first lumen; and a distally-located heat transfer region associated with the body and communicating with the coolant supply and return lumens.

11. The sheath of claim 10, wherein the heat transfer region is established by at least one membrane attached to the body.

12. The sheath of claim 10, wherein the heat transfer region is established by at least one distally-located fluid passageway formed in the body.

13. The sheath of claim 10, further comprising at least one temperature sensor mounted on the body for generating a temperature signal.

14. The sheath of claim 10, wherein the barrier is a septum.

15. The sheath of claim 13, wherein the temperature sensor is thermistor or thermocouple.

16. The sheath of claim 10, in combination with the catheter.

17. The sheath of claim 16, wherein the catheter includes at least one distally-located cooling membrane.

18. The sheath of claim 10, wherein the barrier is a hemostasis valve.

19. An introducer sheath for a central venous catheter, comprising:

a hollow body defining a proximal end, a distal end adapted to be positioned in a patient, and at least one lumen extending between the proximal end and the distal end;

said hollow body further comprising at least one coolant lumen and at least one membrane communicating with the at least one coolant lumen;

a barrier in the lumen at or near the proximal end of the body for selectively blocking the lumen;

at least one temperature sensor mounted on the body at or near the distal end for generating a temperature signal; and a heat transfer region established by one or more heat exchange elements, the heat transfer region extending substantially from the proximal to the distal end of the hollow body.

20. An introducer sheath for a central venous catheter, comprising:

a hollow body defining a proximal end, a distal end adapted to be positioned in a patient, at least one first lumen extending between the proximal end and the distal end, a coolant supply lumen, and a coolant return lumen;

said hollow body further comprising at least one membrane communicating with the coolant supply lumen;

a barrier in the first lumen at or near the proximal end of the body for selectively blocking the first lumen; and a distally-located heat transfer region extending substantially from the proximal end to the distal end of the hollow body and communicating with the coolant supply and return lumens.

21. An introducer sheath for a central venous catheter, comprising:

a hollow body defining a proximal end, a distal end adapted to be positioned in a patient, and at least one lumen means for providing entry for the catheter into a patient's venous system, the lumen means extending between the proximal end and the distal end;

barrier means for selectively blocking the lumen means, the barrier means being disposed at or near the proximal end of the hollow body;

temperature sensor means for generating a temperature signal, the temperature sensor means being disposed on the body at or near the distal end; and a heat transfer region established by at least one heat exchange membrane means for transferring heat between the coolant and fluid in the patient's venous system, the heat transfer region extending substantially from the proximal end to the distal end of the hollow body.

22. The sheath of claim 21, in combination with the central venous catheter.

23. The sheath of claim 22, the catheter including at least one distally-located cooling means for exchanging heat with fluid in the patient's venous system.

24. The sheath of claim 21, the body further including coolant supply means for transporting coolant in a direction from the proximal end to the distal end of the hollow body and coolant return means for transporting coolant in a direction from the distal end to the proximal end of the hollow body, each of the at least one heat exchange means communicating with the coolant supply means and coolant return means.

25. An introducer sheath for a central venous catheter, comprising:

a hollow body defining a proximal end, a distal end adapted to be positioned in a patient, and at least one first lumen means for providing entry for the catheter into a patient's venous system, the at least one first lumen means extending between the proximal end and the distal end, the body also defining a coolant supply means for transporting coolant in a direction from the proximal end to the distal end of the hollow body and a coolant return means for transporting coolant in a direction from the distal end to the proximal end of the hollow body;

barrier means for selectively blocking the first lumen means, the barrier means being disposed at or near the proximal end of the hollow body; and a heat transfer region established by at least one heat exchange membrane means for transferring heat between the coolant and fluid in the patient's venous system, the heat transfer region extending substantially from the proximal end to the distal end of the hollow body, each of the at least one heat exchange means communicating with the coolant supply means and coolant return means.

26. The sheath of claim 25, in combination with the catheter.

27. The sheath of claim 26, the catheter including at least one distally-located cooling means for exchanging heat with fluid in the patient's venous system.

* * * * *